United States Patent [19]
Cohen

[11] Patent Number: 5,156,148
[45] Date of Patent: * Oct. 20, 1992

[54] SYSTEM FOR TREATING A MALFUNCTIONING HEART

[75] Inventor: Todd J. Cohen, San Francisco, Calif.

[73] Assignee: Leonard Bloom, Towson, Md.; a part interest

[*] Notice: The portion of the term of this patent subsequent to May 14, 2008 has been disclaimed.

[21] Appl. No.: 699,472

[22] Filed: May 13, 1991

Related U.S. Application Data

[63] Continuation-in-part of Ser. No. 416,024, Oct. 2, 1989, Pat. No. 5,014,698, which is a continuation-in-part of Ser. No. 385,544, Jul. 27, 1989, Pat. No. 4,984,572, which is a continuation of Ser. No. 233,367, Aug. 18, 1988, Pat. No. 4,967,749, which is a continuation-in-part of Ser. No. 105,030, Oct. 6, 1987, Pat. No. 4,774,950.

[51] Int. Cl.⁵ ............................................... A61N 1/00
[52] U.S. Cl. .................... 128/419 PG; 128/419 D
[58] Field of Search ........... 128/419 D, 419 B, 419 P, 128/419 PG

[56] References Cited

U.S. PATENT DOCUMENTS

| | | | |
|---|---|---|---|
| 3,614,955 | 10/1971 | Mirowski | 128/419 D |
| 3,866,615 | 2/1975 | Hewson | 128/419 PG |
| 3,878,564 | 4/1975 | Yao et al. | 128/419 B |
| 4,774,950 | 10/1988 | Cohen | 128/419 D |
| 4,799,493 | 1/1989 | DuFault | 128/419 D |
| 4,807,629 | 2/1989 | Baudino et al. | 128/419 PG |
| 4,819,662 | 4/1989 | Heil, Jr. et al. | 128/419 P |
| 4,869,252 | 9/1989 | Gilli | 128/419 D |

Primary Examiner—William E. Kamm
Assistant Examiner—George Manuel
Attorney, Agent, or Firm—Leonard Bloom

[57] ABSTRACT

A system for treating the malfunctioning heart of a patient includes means which derive at least one electrical signal from the patient's heart and means which derive at least one physiologic signal from or related to the patient's circulatory system. A central processing unit, which may be a programmable microprocessor, with a RAM and a ROM, receives and responds to the at least one electrical signal and to the at least one physiologic signal. Output means, which may include a heart assist pump, pacers, drug delivery devices and cardioverting/defibrillating apparatuses, controlled by the central processing unit provides corrective measure(s) to the patient. Adjustable or variable baselines, against which a representation of the current, short-term magnitude of the selected physiologic parameter or parameters are provided. The variable baseline(s) is (are) a representation of the selected physiologic parameter(s) determined over a long term of greater duration than the short term over which the current magnitude(s) of the parameter(s) is (are) measured.

104 Claims, 15 Drawing Sheets

SYSTEM FOR TREATING A MALFUNCTIONING HEART

CROSS REFERENCE TO RELATED APPLICATION

This application is a continuation-in-part of copending application Ser. No. 416,024 (now U.S. Pat. No. 5,014,698 granted May 14, 1991) of Todd J. Cohen filed Oct. 2 1989 and entitled "Method of and System for Monitoring and Treating a Malfunctioning Heart". The U.S. Ser. No. 416,024 application, in turn, is a continuation-in-part of application U.S. Ser. No. 385,544, which has matured as U.S. Pat. No. 4,984,572 granted Jan. 15, 1991, of Todd J. Cohen filed Jul. 27, 1989 and entitled "Hemodynamically Responsive System for and Method of Treating a Malfunctioning Heart" which is a continuation of U.S. Ser. No. 233,367, which has matured as U.S. Pat. No. 4,967,749 issued Nov. 6, 1990, of Todd J. Cohen filed Aug. 18, 1988 and entitled "Hemodynamically Responsive System for and Method of Treating a Malfunctioning Heart" which is a continuation-in-part of U.S. Ser. No. 105,030 of Todd J. Cohen filed on Oct. 6, 1987 and entitled "Hemodynamically Responsive System for and Method of Treating a Malfunctioning Heart", which has matured as U.S. Pat. No. 4,774,950 granted Oct. 4, 1988. The disclosures of the prior applications are incorporated herein in their entirety respectively by reference.

BACKGROUND OF THE INVENTION

1. Field of the Invention

This invention relates to a system for treating a malfunctioning heart. The invention provides for the cardioverting/defibrillation of a malfunctioning heart, as well as the possibility of overcoming a tachycardia and bradycardia manifestations without resorting to either cardioverting or defibrillating the heart. The invention also may involve sensing and treating asystole, ischemia, early infarction and heart failure.

2. Description of the Prior Art

In recent years, substantial progress has been made in pacemakers and in the development of cardioverting/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping below a fixed predetermined level and not returning above the predetermined level for a given period of time.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a predetermined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

The U.S. Pat. No. 4,770,177 of Schroeppel discloses a pacer which paces a heart in accordance with the heart/pacer rate needed to produce a required cardiac output while a person is exercising or undergoes emotional stress in response to changes in venous blood vessel diameter. The pacer is adapted to be implanted in a human body and has a pulse generator and control circuitry, which may be realized by a microprocessor. A pacing lead adapted to be implanted in a heart has a tip electrode adapted to engage and supply pacing pulses to a right ventricle of a heart. A piezoelectric sensor determines changes in a diameter of a vein in the human body. Computing circuitry, including the control circuitry, relates the changes in venous blood vessel diameter with the required pacing rate needed to supply a desired cardiac output, and causes the pacer to pace the heart at the required rate when the heart is not naturally paced. The pacer of Schroeppel is not combined with any cardioverter/defibrillator.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. This cardioverter-defibrillator has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", *Medical Instrumentation*, Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461–466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made to correct the ischemia (in a closed-loop fashion). Closed loop intravenous drug delivery systems have been developed (and are undergoing evaluation) for the treatment of heart failure. Such systems could be incorporated into an inplantable device to permit the delivery of electrical therapy (pacing/cardioversion/defibrillation) as well as drug therapy, to correct a malfunctioning heart.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with many current systems is that they function primarily as a rate-only sensing systems and may fire for nonmalignant as well as malignant tachycardias. These firings are not benign; potentially endangering myocardium wasting energy and inflicting pain on the conscious patient, all distinct shortcomings and disadvantages.

External ST segment monitoring systems are commercially available. These systems compare the normal or baseline ST segment of an ECG to that during normal exercise or activity to determine whether the change is significant and indicative of ischemia. Such monitoring systems are currently worn on the patient's waist or over the shoulders, and no active treatment is offered (since ischemia is only identified after the recording is complete, and the tape is scanned). It is possible that this information can be acquired in real time, such that appropriate drug therapy could be delivered to correct the ischemia (in a closed-loop fashion). Closed loop intravenous drug delivery systems have been developed (and are undergoing evaluation) for the treatment of heart failure. Such systems could be incorporated into an inplantable device to permit the delivery of electrical therapy pacing/cardioversion/defibrillation) as well as drug therapy, to correct a malfunctioning heart.

SUMMARY OF THE INVENTION

The principle object of the present invention is to provide a system for treating a malfunctioning heart which provides for determining the presence of a malfunction and deliver an output to correct or alleviate the malfunction.

A further object of the present invention is to provide a system for treating a malfunctioning heart which is physiologically responsive to change in at least one physiologic parameter, such as pressure(s) at one or more sites in the circulatory system of a patient, and to an electrical signal or signal derived from the heart.

Another object of the present invention is to provide an implantable system for treating a malfunctioning heart which achieves the above-stated objects.

As used herein, the term physiologic parameter means any parameter which is derived from the human body which relates information and reflects the hemodynamic rate or condition of the patient. This term includes information which may be derived from a biosensor (or biosensors) or a characteristic of an electrical signal other than rate which relates hemodynamic information. An example would be the determination of ST signal changes from the electrical signal as a physiologic parameter which indicates ischemia.

From one vantage point, the invention can be seen as being in a system for treating the malfunctioning heart of a patient. Means derive at least one electrical signal from the patient's heart. Other means derive at least one physiologic signal from or related to the patient's circulatory system. A central processing unit, which may be a microprocessor, with its associated RAM and ROM is provided. Means input the at least one electrical signal and the at least one physiologic signal to the central processing unit. Output means controlled by the central processing unit provide a corrective measure or measures to the patient. The system can be an implantable system or an external system or a hybrid. For example, the sensing device and/or electrodes and/or the shock delivering electrodes may be implantable, while the pulse generating and signal processing circuitry may be external. The electrodes may be intracardiac electrodes. The central processing unit may effect a determination of both a long-term level and a current, short-term level for the selected physiological parameter and a comparison of one to the other.

From a slightly different viewpoint, the invention can be seen as being in a system for treating the malfunctioning heart of a patient which includes means for deriving at least one electrical signal from the patient's heart and means for deriving at least one physiologic signal from or related to the patient's circulatory system. A central processing unit, associated with a ROM and RAM, is provided. Means the at least one electrical signal and the at least one physiologic signal to the central processing unit. Monitoring and/or recording means are associated with the central processing unit to provide indications of the inputs and outputs thereof. Here again, the system can be an implantable system or an external system or a hybrid. The central processing unit may effect a determination of both a long-term level and a current, short-term level for the selected physiological parameter and a comparison of one to the other.

The system may include means for monitoring heart rhythm to develop the at least one electrical signal, and respectively and/or in various combinations means responsive to the at least one electrical signal and to the at least one physiologic signal for identifying stable SVT, unstable SVT, stable VT, unstable VT, stable atrial fibrillation, unstable atrial fibrillation, ventricular fibrillation, asystole, stable bradycardia, unstable bradycardia, ischemia, early infarction and heart failure alone. Here again, the system may be an implantable system or an external system or a hybrid. The central processing unit may effect a determination of both a long-term level and a current, short-term level for the selected physiological parameter and a comparison of one to the other.

The invention can also be viewed as a system for treating the malfunctioning heart of a patient, which includes, combination, means for deriving at least one electrical signal from the patient's heart and means for deriving at least one physiologic signal from or related to the patient's circulatory system. Means responsive to the physiologic signal determine when a change in a physiologic parameter of at least a predetermined magnitude from a baseline for the parameter occurs. A central processing unit controls delivery of a selected heart-malfunction-corrective input or inputs to the patient. Circuitry is provided for inputting the at least one electrical signal and the at least one physiologic signal to the central processing unit. Output means, including defibrillating means, controlled by the central processing unit provide at least one heart-malfunction-corrective input to the patient from among a plurality of the heart-malfunction-corrective inputs, whereby malfunctions of the heart may be corrected. The central processing unit may effect a determination of both a long-term level and a current, short-term level for the selected physiological parameter and a comparison of one to the other.

Ischemia may be detected by comparing short-term changes in the ST segment of the ECG to long-term (or baseline) ST segment. The time response of the physiologic signal together with the behavior of the ECG signal could indicate the presence and degree of heart failure as well as myocardial infarction. These features, together with heart rhythm control system provide a novel method for treating a malfunctioning heart.

The novel features that are considered characteristic of the invention are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

DETAILED DESCRIPTION OF THE PREFERRED EMBODIMENTS

Figure 1:
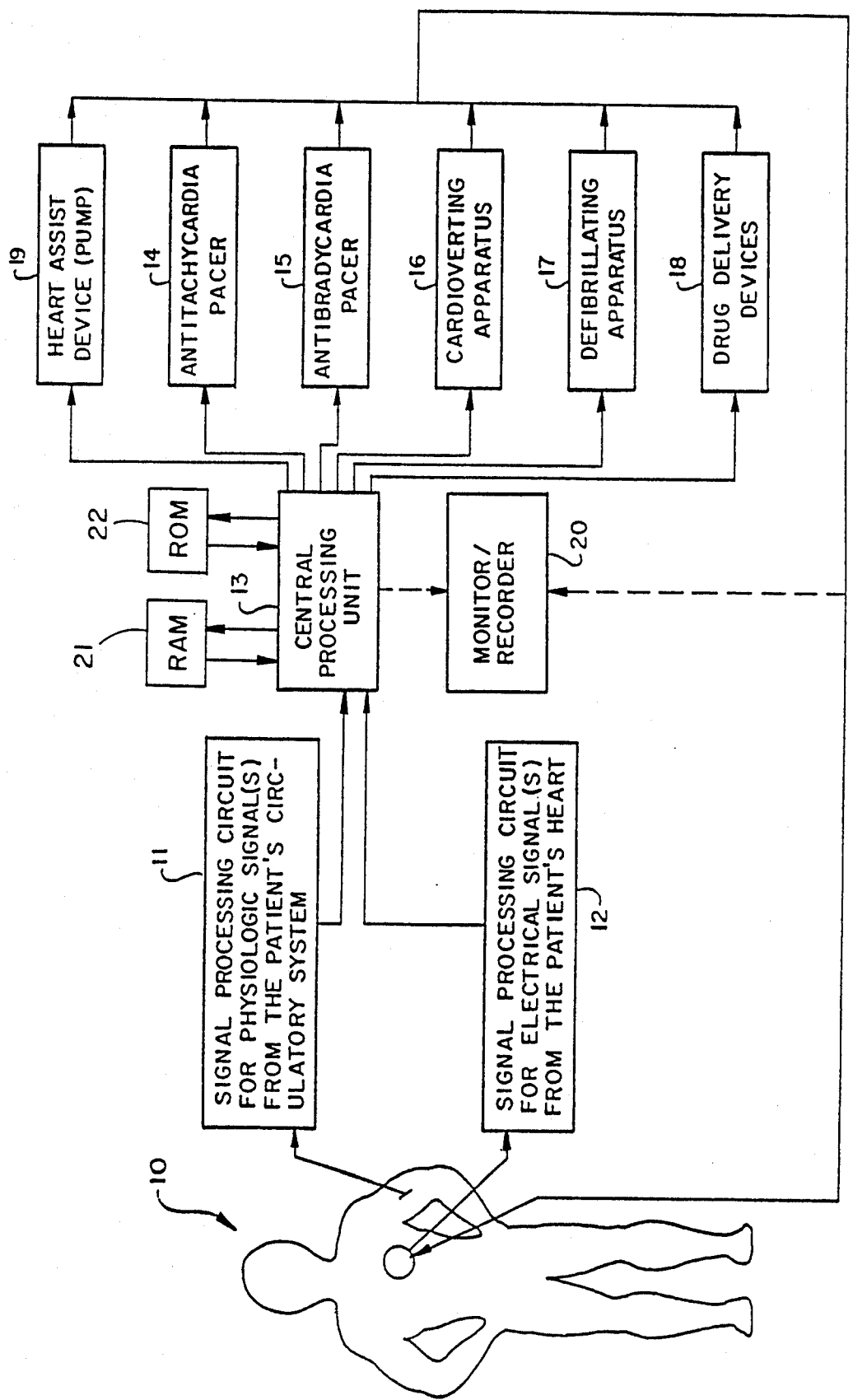
FIG. 1 is a block, generalized illustration of an exemplary, first embodiment of an electrical- and physiologic- signal responsive system for treating a malfunctioning heart in accordance with the present invention.

As illustrated in FIG. 1, an exemplary system for treating a malfunctioning heart of a patient 10 includes a signal processing circuit 11 which receives signals representing a physiologic condition at one or more sites within or related to the circulatory system of a patient. The signal(s) representing the physiologic condition(s) preferably involve hemodynamic parameter(s) at the site(s) and reflect the dynamic nature of the pressure(s) at the site(s). The system also includes a signal processing circuit 12 which receives an electrical signal or signals from the heart of a patient; for example, the circuit 12 may receive an electrical signal or signals obtained by conventional internal or external EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a programmable microprocessor, with an associated ROM 22 and a RAM 21.

Preferably, the system illustrated in FIG. 1 includes a monitor/recorder 20, which may provide a visual and/or audible readout to aid medical personnel providing treatment for he patient. The monitor/recorder 20, as is known, may also effect recording, on strip graphs or the like, of the signals fed to the central processing unit 13, as well as the command signals from the central processing unit, which it generates in response to the physiologic signal(s) and the electrical signal(s) supplied thereto.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the electrical signal(s) and the physiologic signal(s) from the signal processing circuits 11 and 12, in the event no malfunction of the heart of the patient 10 has been identified.

The signal(s) from the signal processing circuit 13 may be processed by the central processing unit 13 to derive varying, long-term baseline(s) for the physiologic parameter(s) against which current, short-term magnitude(s) of the physiologic parameter(s) is (are) to be compared. In another embodiment, the programmable central processing unit 13, in conjunction with its associated RAM 21 and ROM 22, may develop a fixed baseline or baselines, which is or are adjustable and against which the selected physiologic parameter or parameters may be compared.

In the event a malfunction of the heart of the patient 10 is identified by the central processing unit 13, the central processing unit supplies an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17 drug delivery devices 18, and a heart-assist device 19, which may be an assist pump or a similar device. It is to be appreciated that cardioverter and defibrillator may share components and be constructed as illustrated in U.S. Pat. No. 4,774,950.

The malfunction correcting circuits 14–17 produce respective malfunction correcting electrical output signals, which are delivered to the patient 10 as required. The drug delivery devices 18 which may consist of a number of pumps or other drug delivery devices, such as gravity operated delivery systems supply medications to the patient 10 in an effort to overcome or correct the malfunction. The heart-assist device 19, which may be a pump, when energized, aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Figure 2:
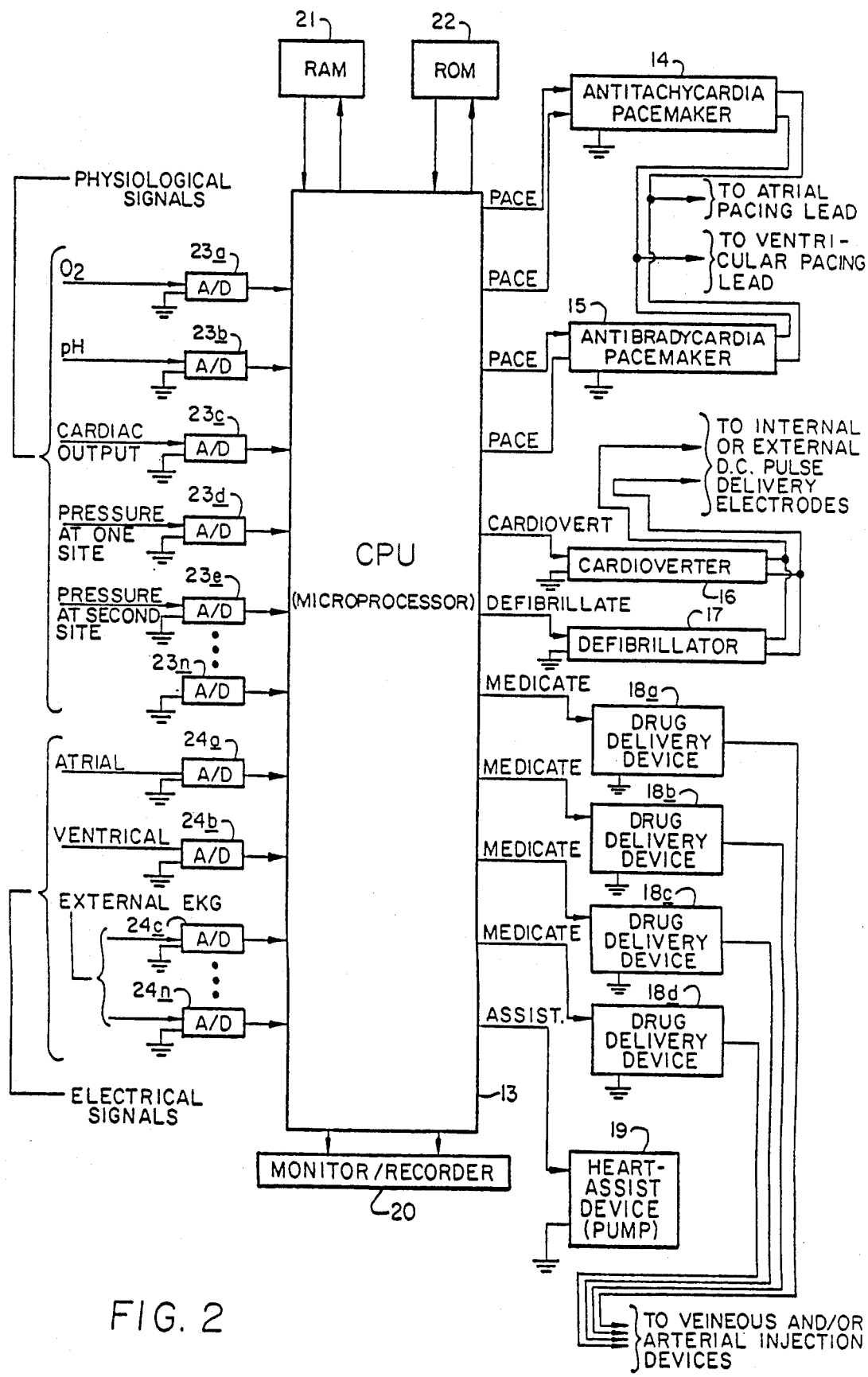
FIG. 2 is a more detailed illustration of the exemplary system shown in FIG. 1 for treating a malfunctioning heart.

As illustrated in FIG. 2, the first preferred detailed embodiment, like the more generalized illustration thereof shown in FIG. 1, is provided with a CPU 13 and its associated RAM 21 and ROM 22. If desired inputs and outputs to and from the CPU 13 may be fed to a monitor/recorder 20.

The input side of the system, includes a plurality of physiologic signals, actually electric analogue signal representations of physiologic conditions, shown by way of example as $O_2$ level in mixed venous blood, pH of blood, cardiac output, pressure at one site in the circulatory system of the patient and pressure at another site in the circulatory system of the patient. Other possible signals could represent $CO_2$ level in blood, end tidal $CO_2$ level in blood, DP/dt, blood temperature, body temperature, respiratory rate and lactic acidosis, to name a few. The respective physiologic signals are converted into digital signals by respective analogue-to-digital converters 23a to 23n and supplied as distinct inputs to the CPU 13.

The system of FIG. 2 includes electrical signals derived from action of the patient's heart. The electrical signals, as illustrated, include an atrial signal, a ventricular signal and a plurality of EKG signals, which are obtained by conventional means. The respective electrical signals are fed to respective analogue-to-digital converters 24a–24n and are converted into respective digital signals which are fed, as distinct inputs, to the CPU 13.

The CPU 13 effects a comparison of one or more of the digital signal representations of the physiologic signals against a fixed (for example, as disclosed in U.S. Pat. No. 4,967,749) or a varying baseline (for example, as disclosed in U.S. Pat. 4,774,950) representations thereof, possibly after processing the signals into signals representing mean, systolic, diastolic, pulse pressures or the like. The CPU 13 also determines the pulse rate, R-wave, QRS complex (possibly against a "template" of the patient's QRS complex when the heart is functioning properly) and/or another morphologic basis, tachycardia acceleration, atrial-ventricular timing, ST segment analysis and the like.

The CPU 13, using programs stored in the ROM 21, determines if any of the malfunctions set out in FIGS. 5A-5I is present and produces control signals which are fed respectively to the antitachycardia pacemaker 14, to the antibradycardia pacemaker 15, to the cardioverter 16, to the defibrillator 17, to the respective drug delivery devices 18a–18d and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia. The diagnostic and treatment routines which are carried out by the central processing unit 13, with its associated RAM 21 and ROM 22, are set out in blocks 500–599 of FIGS. 5A-5I.

Figure 3:
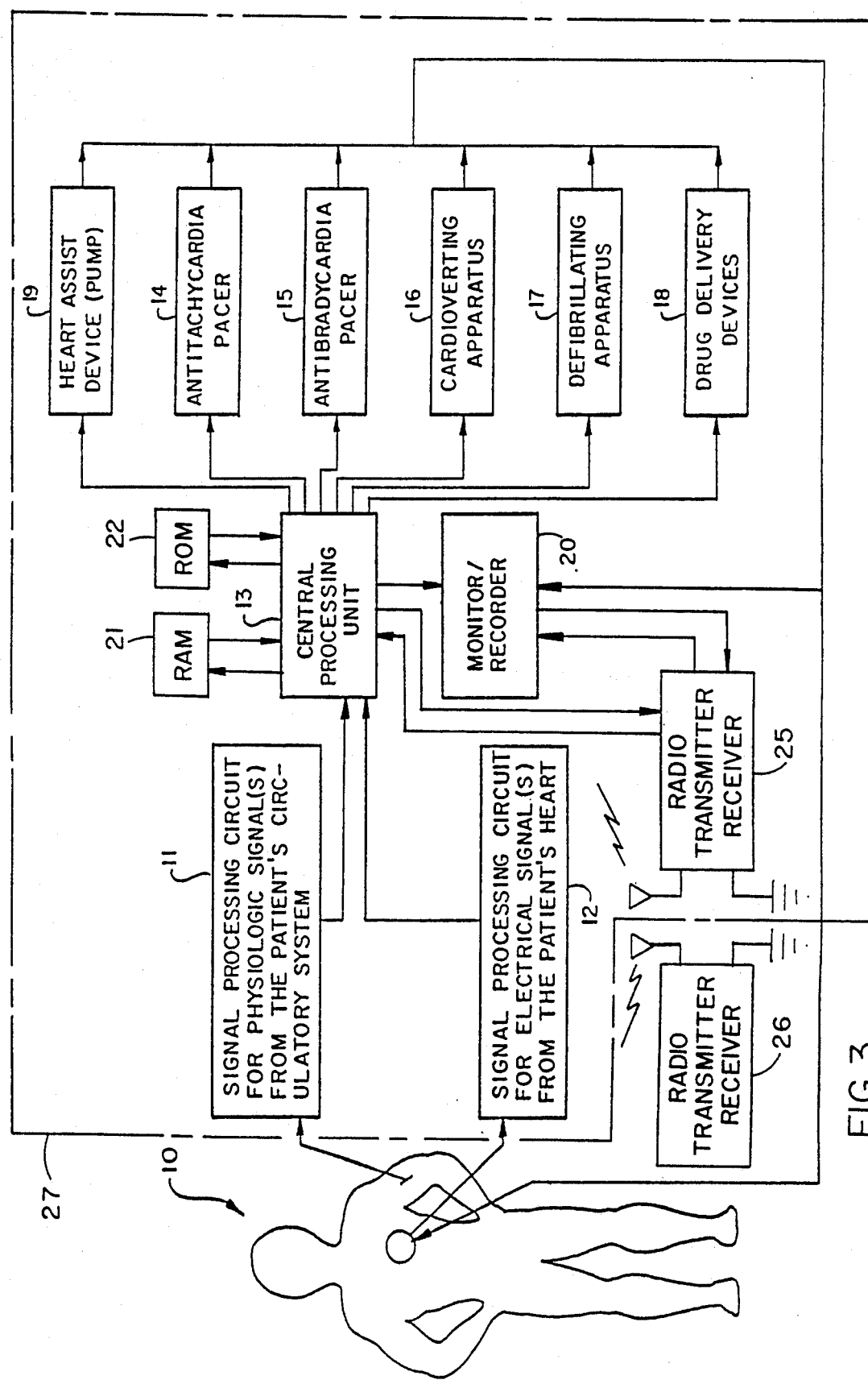
FIG. 3 is a block, generalized illustration of an exemplary, second embodiment of an electrical- and physiologic- signal responsive system for treating a malfunctioning heart in accordance with the present invention.

As illustrated in FIG. 3, an exemplary system for treating a malfunctioning heart of a patient 10 includes an implantable portion 27. The implantable portion 27 comprises a signal processing circuit 11 which receives signals representing a physiologic condition at one or more sites within or related to the circulatory system of a patient. The signal(s) representing the physiologic condition(s) preferably involve hemodynamic parameter(s) at the site(s) and reflect the dynamic nature of the pressure(s) at the site(s). The system also includes a signal processing circuit 12 which receives an electrical signal or signals from the heart of a patient; for example, the circuit 12 may receive an electrical signal or signals obtained by conventional internal EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a programmable microprocessor, with an associated a ROM 22 and a RAM 21.

Preferably, the system illustrated in FIG. 3 includes a monitor/recorder 20, which is coupled with a radio transmitter-receiver 25 and which, upon a command signal from the receiver portion of the transmitter-receiver 25, will respond to commands and feed to the transmitter portion of the transmitter-receiver 25 signals representing stores the signals fed to the central processing unit 13, as well as the command signals from the central processing unit, which it generates in response to the physiologic signal(s) and the electrical signal(s) supplied thereto, and signals representing the presence or absence of output from the respective devices 14–19. The implanted radio transmitter-receiver 25 is coupled to a radio transmitter-receiver 26, the transmitter portion of which provides command signals to the radio transmitter 25 to effect recall of data stored in the monitor/recorder 20. The transmitter-receiver 25 and the transmitter-receiver 26 may be used to effect a reprogramming of the CPU 13 with its associated RAM 21 and ROM 22, if desired to change or to set the baselines, therapy delivery routines and the like. Of course, magnetic or ultrasonic links could be used instead of the radio link. It is to be understood that in some practical realization of the system the monitor/recorder 20 functions could be carried out by dedicated portions of the RAM 21 and ROM 22 or a special storage member in or associated with the central processing unit 13.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the electrical signal(s) and the physiologic signal(s) from the signal processing circuits 11 and 12, in the event no malfunction of the heart of the patient 10 has been identified.

The signal(s) from the signal processing circuit 13 may be processed by the central processing unit 13 to derive varying, long-term baseline(s) for the physiologic parameter(s) against which current, short-term magnitude(s) of the physiologic parameter(s) is (are) to be compared. In another embodiment, the programmable central processing unit 13, in conjunction with its associated RAM 21 and ROM 22, may develop a fixed baseline or baselines, which is or are adjustable and against which the selected physiologic parameter or parameters may be compared.

In the event a malfunction of the heart of the patient 10 is identified by the implanted central processing unit 13, the central processing unit supplies an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17 drug delivery devices 18, and a heart-assist device 19, which may be an assist pump or a similar device. It is to be appreciated that cardioverter and defibrillator may share components and be constructed as illustrated in U.S. Pat. No. 4,774,950.

The malfunction correcting circuits 14–17 produce respective malfunction correcting electrical output signals, which are delivered to the patient 10 as required. The drug delivery devices 19 which may consist of a number of pumps or other drug delivery devices, such as gravity operated delivery systems supply medications to the patient 10 in an effort to overcome or correct the malfunction. The heart-assist device 19, which may be a pump, when energized, aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Figure 4:
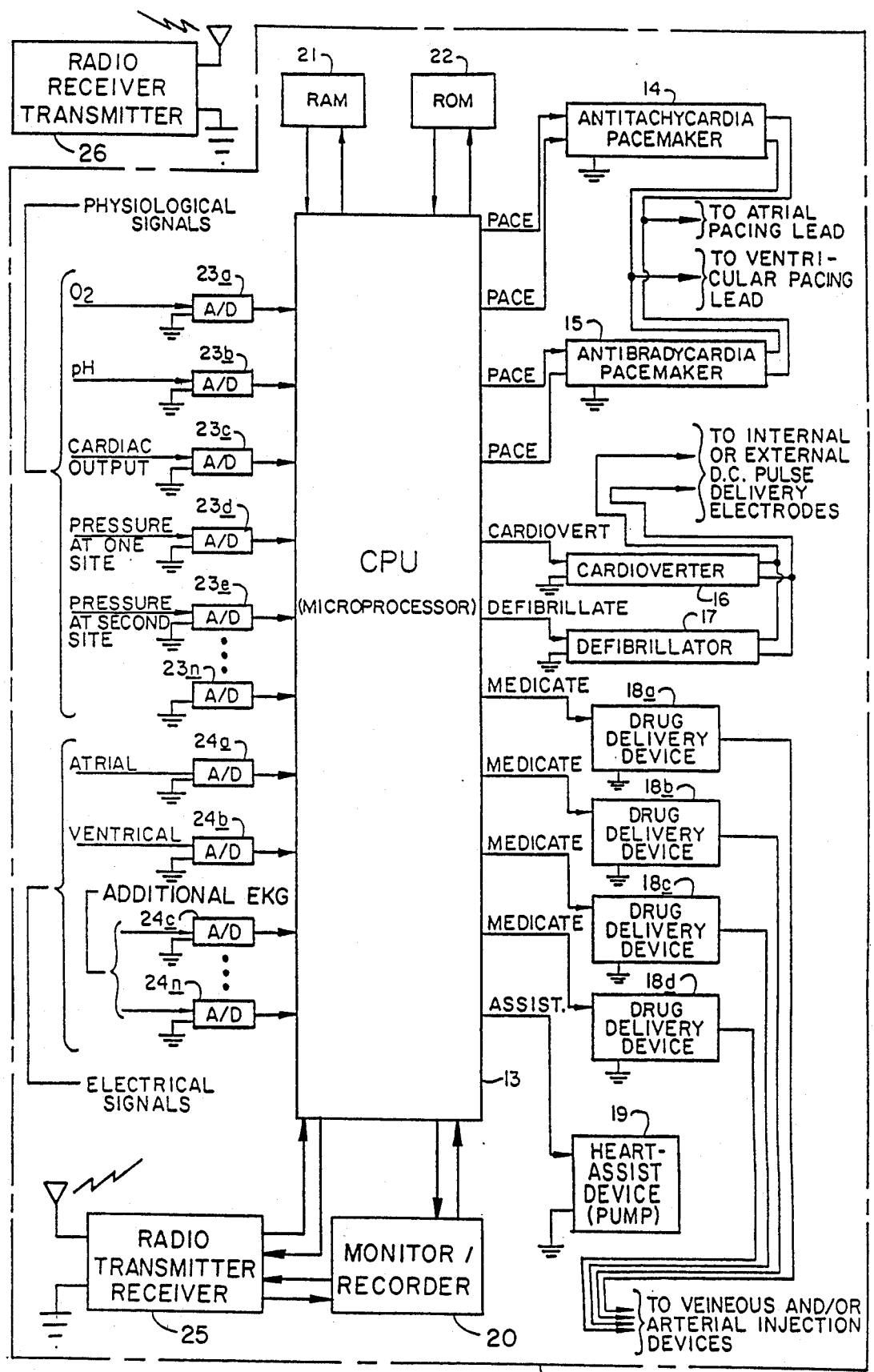
FIG. 4 is a more detailed illustration of the exemplary system shown in FIG. 3 for treating a malfunctioning heart in accordance with the present invention.
Figure 5A:
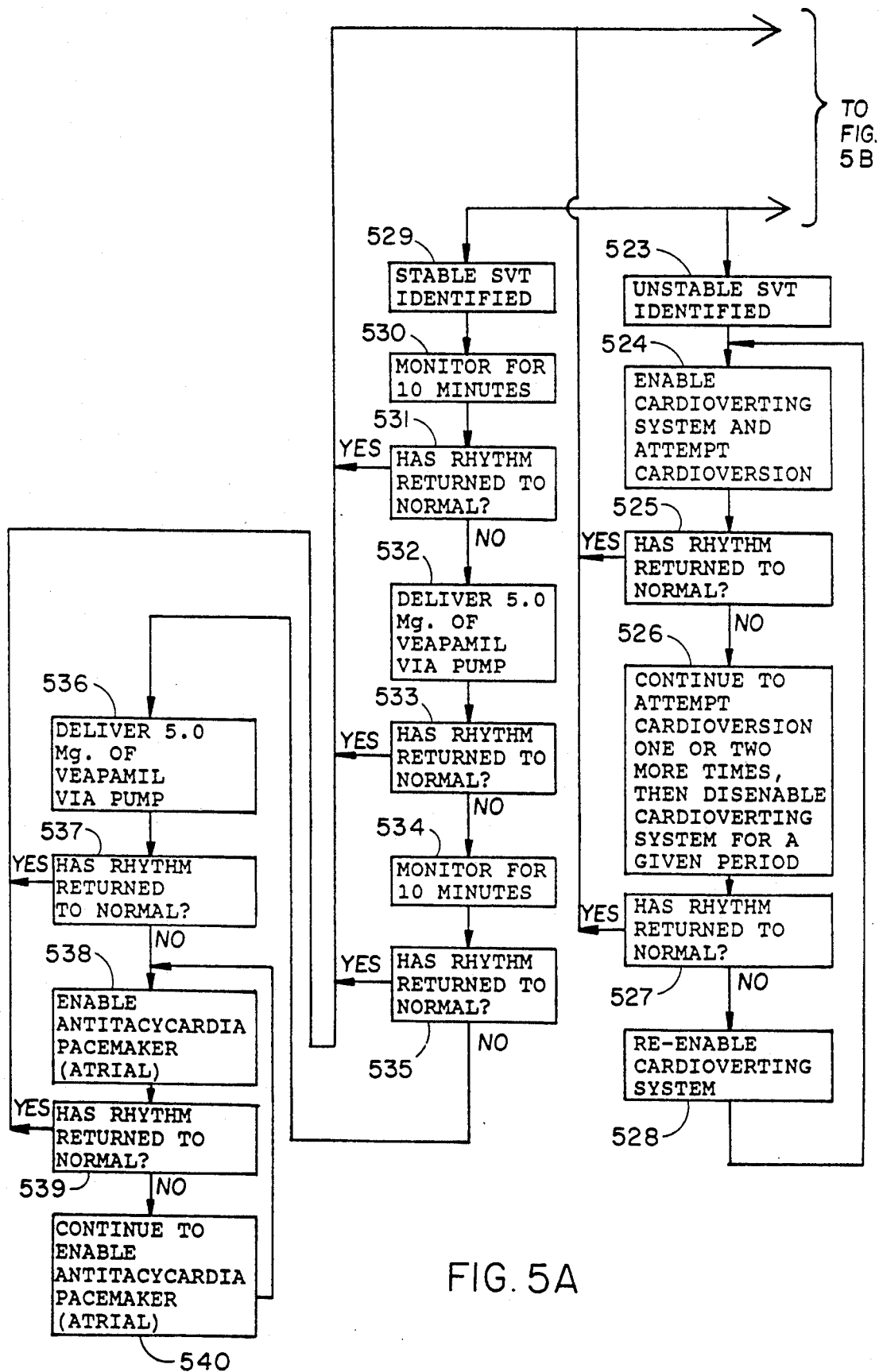
FIGS. 5A-5I, when taken together, constitute a flow chart of steps which may be executed by the systems illustrated in FIGS. 1, 2 and 3, 4.
Figure 5B:
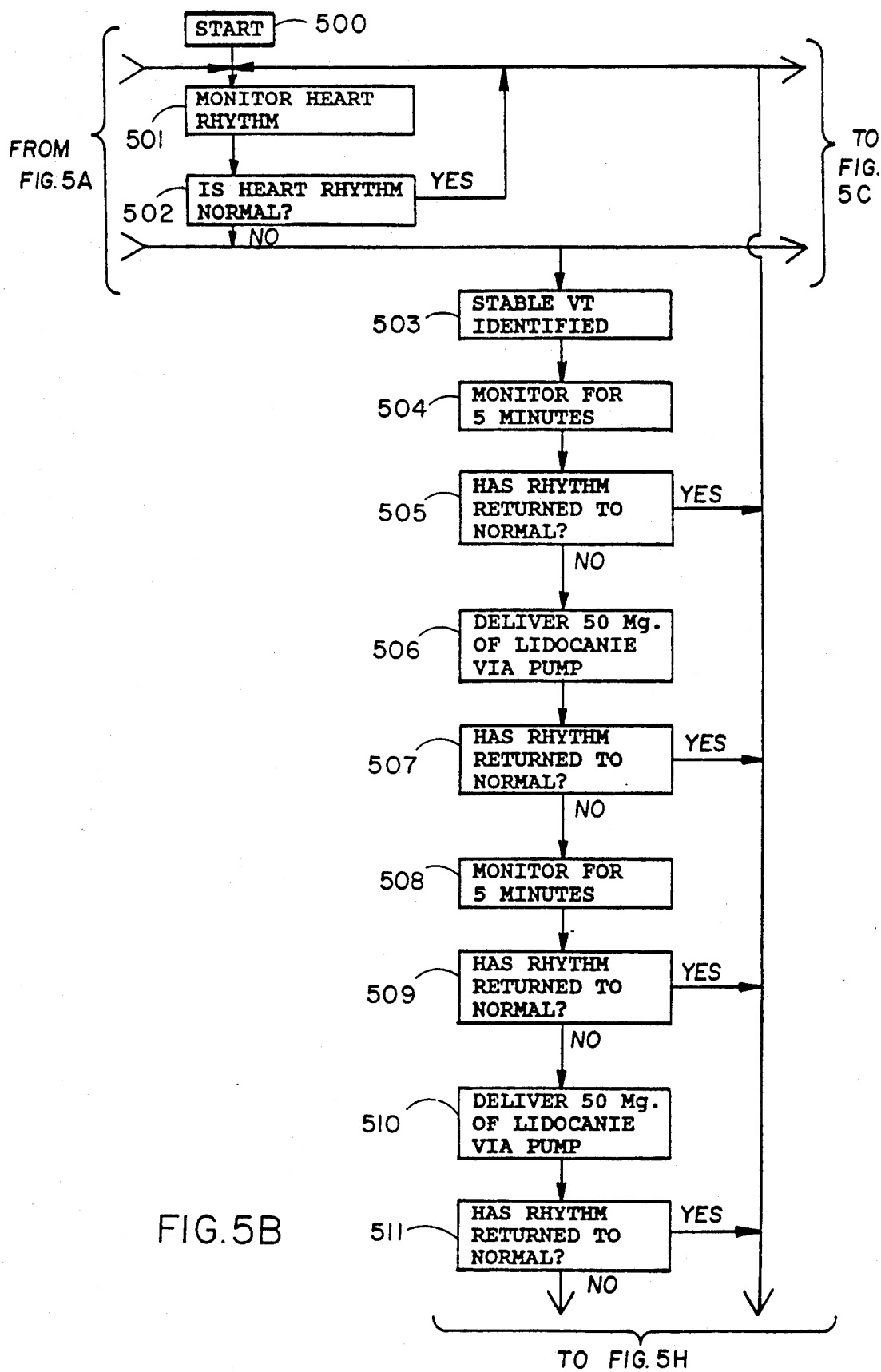
Figure 5C:
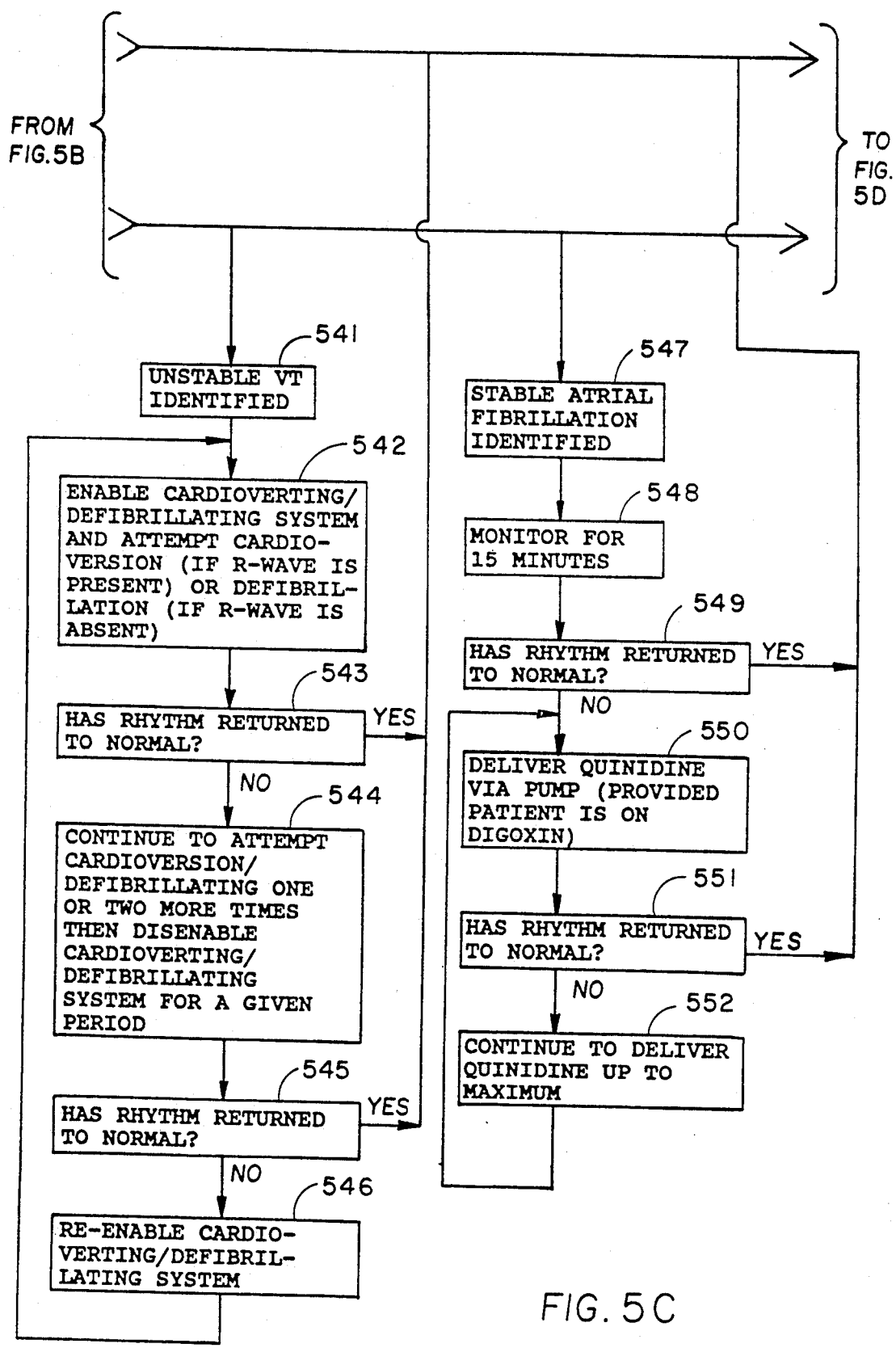
Figure 5D:
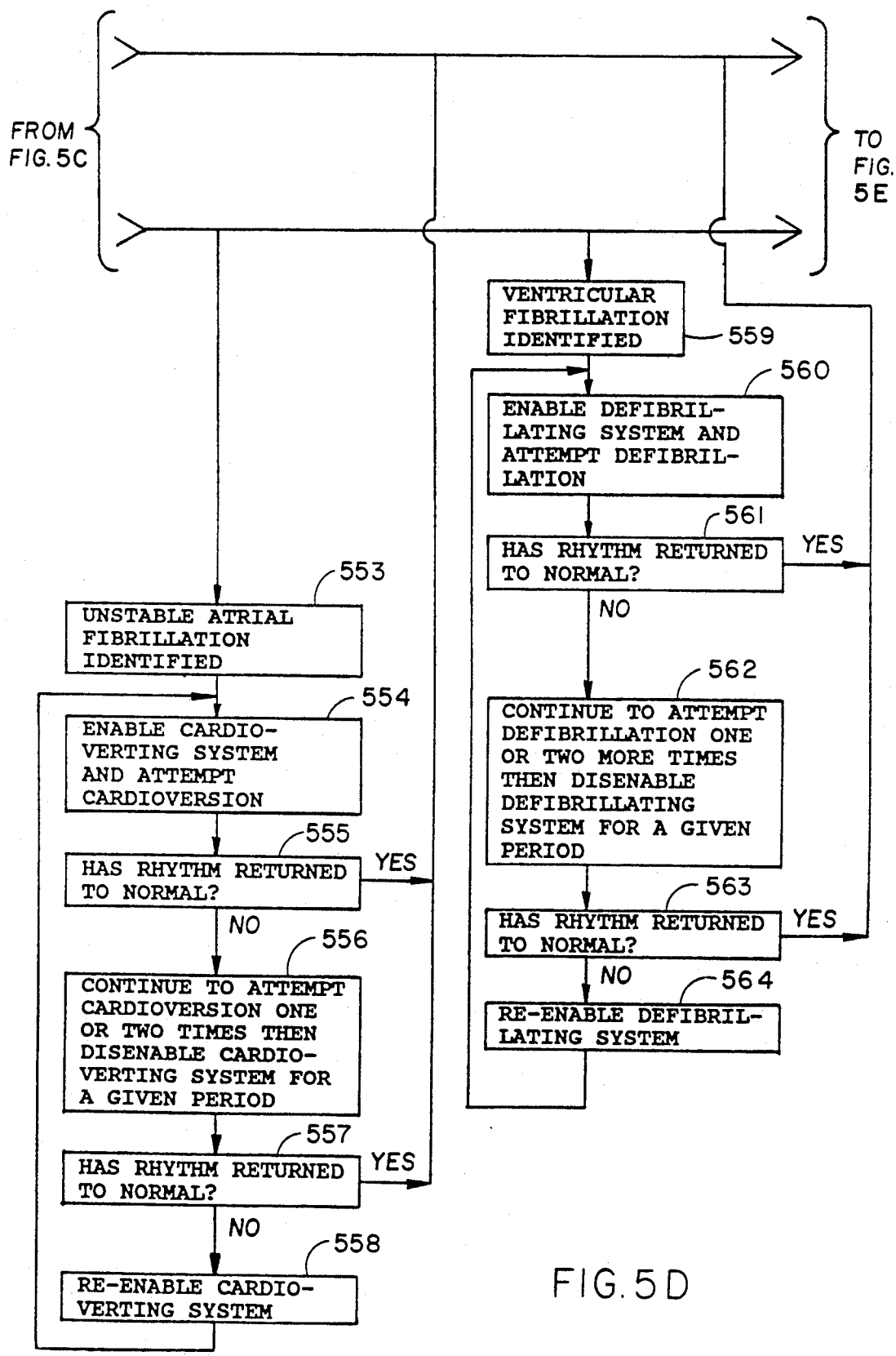
Figure 5E:
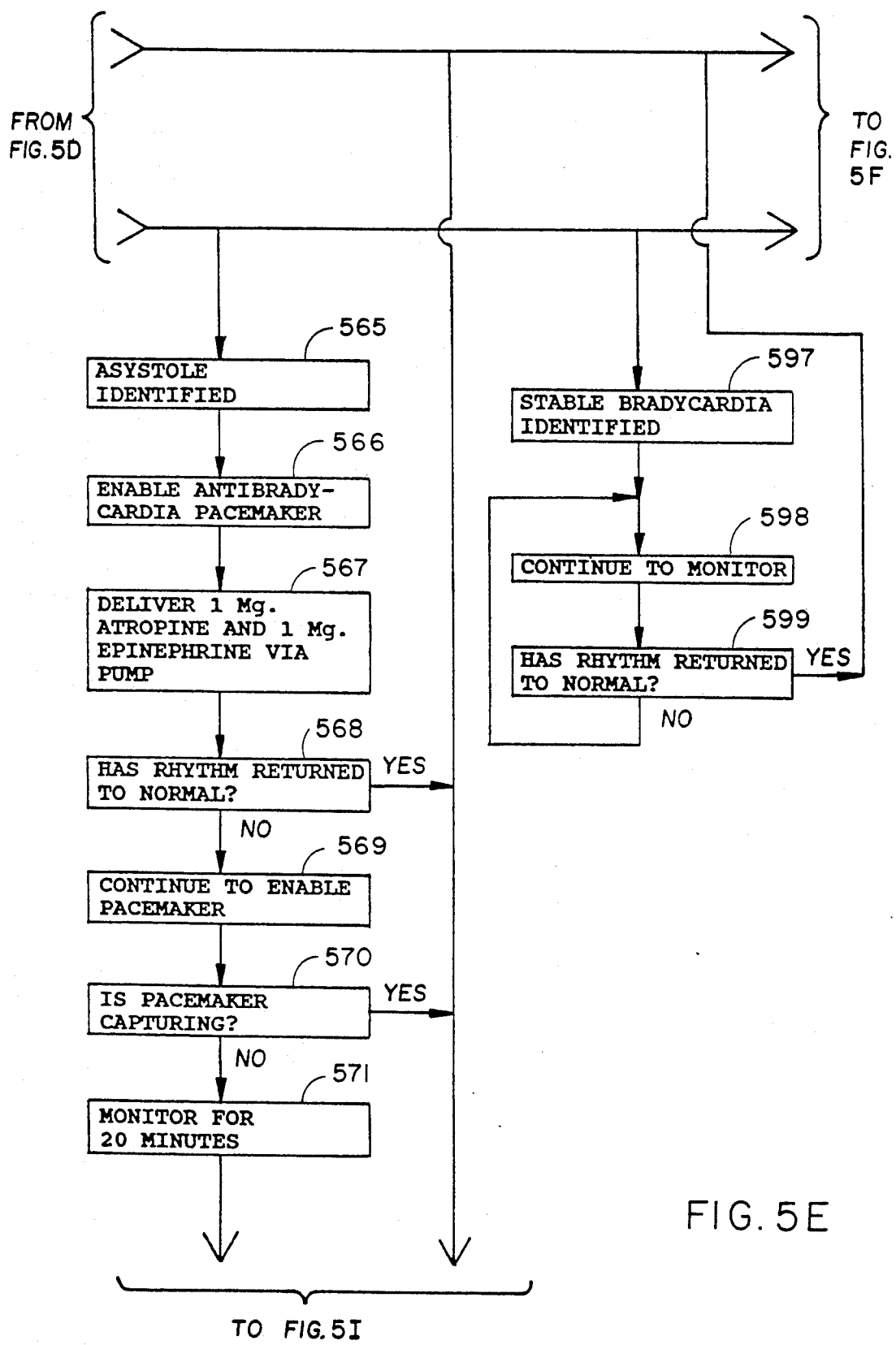
Figure 5F:
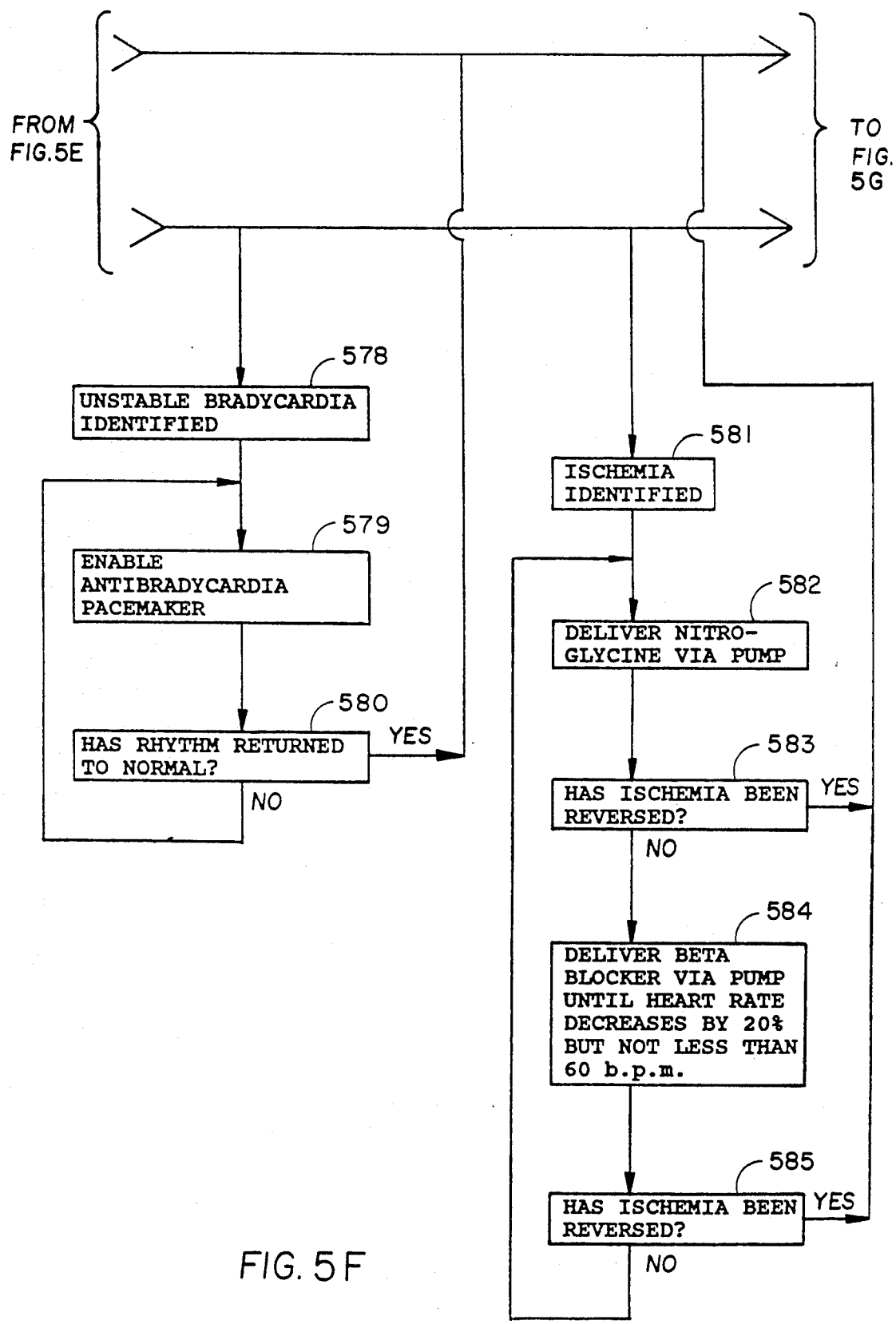
Figure 5G:
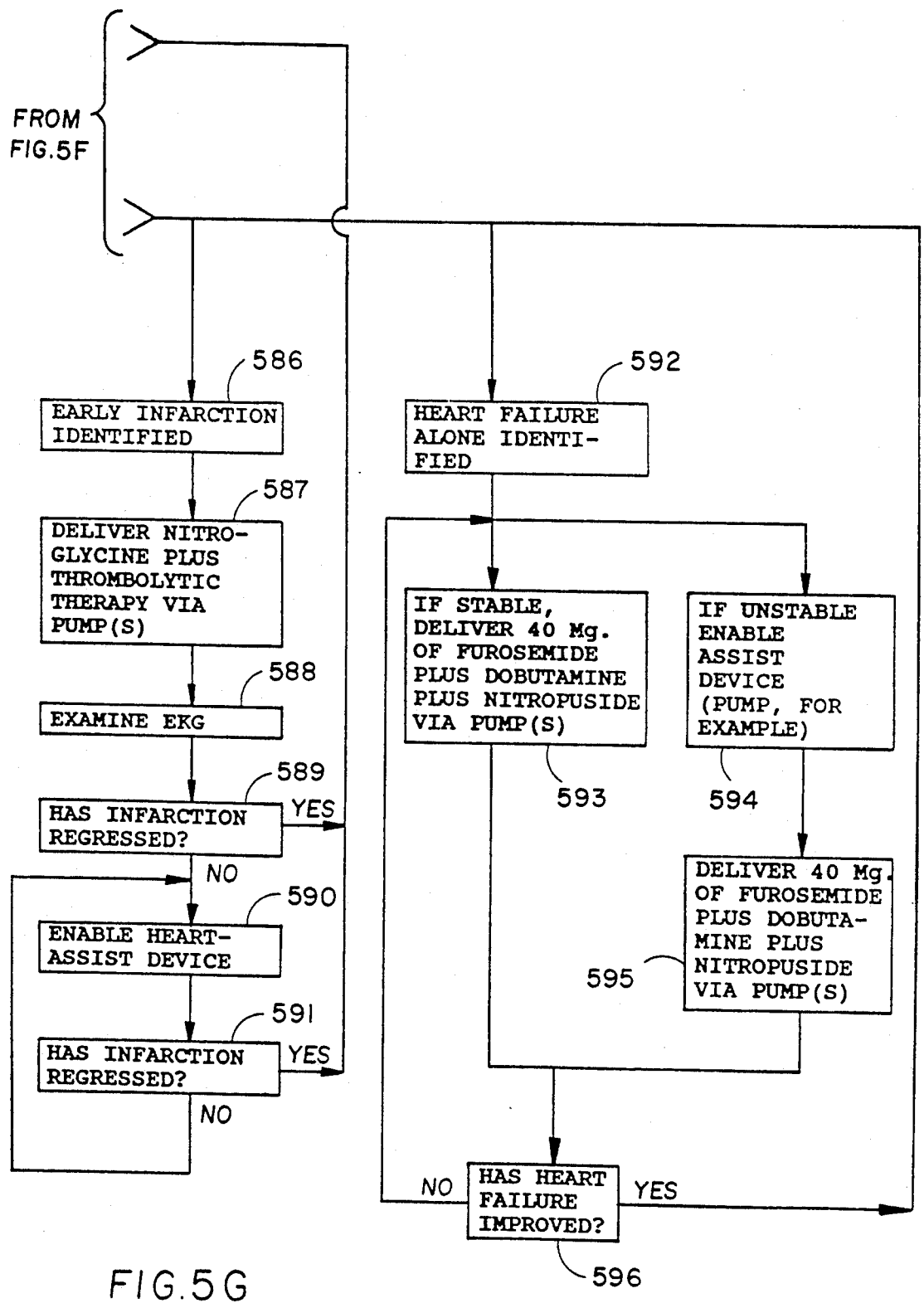
Figure 5H:
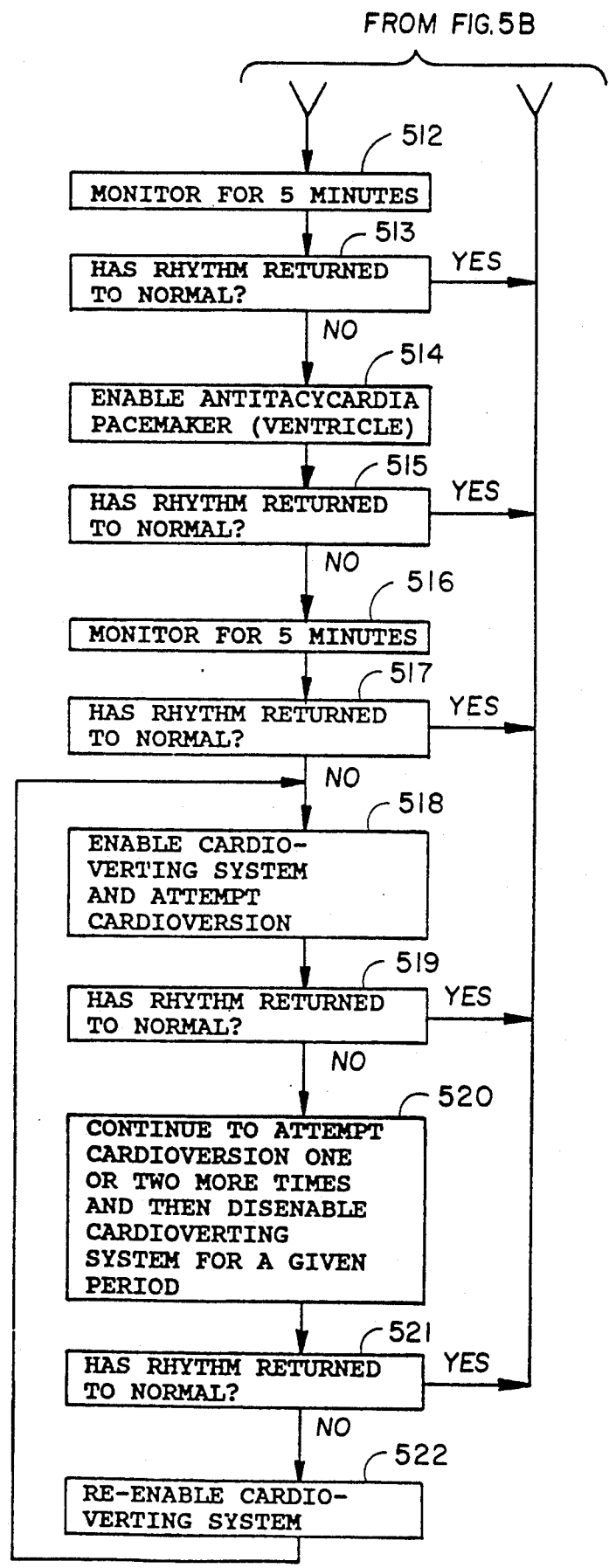
Figure 5I:
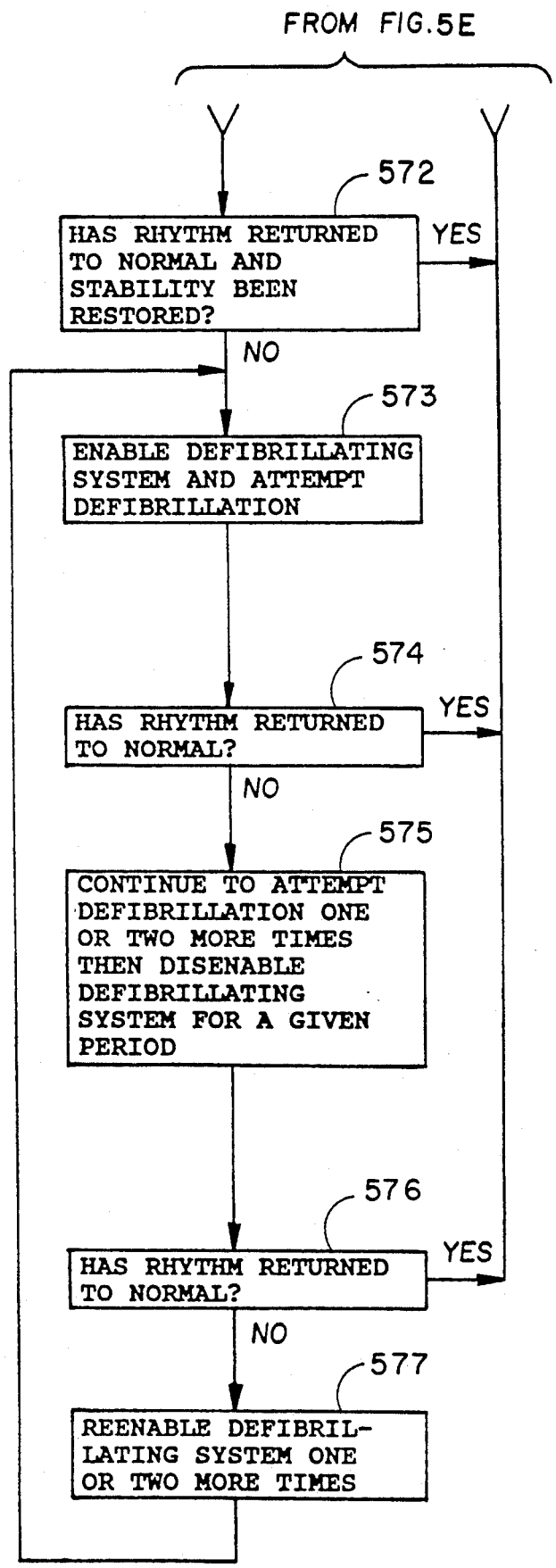
Figure 6:
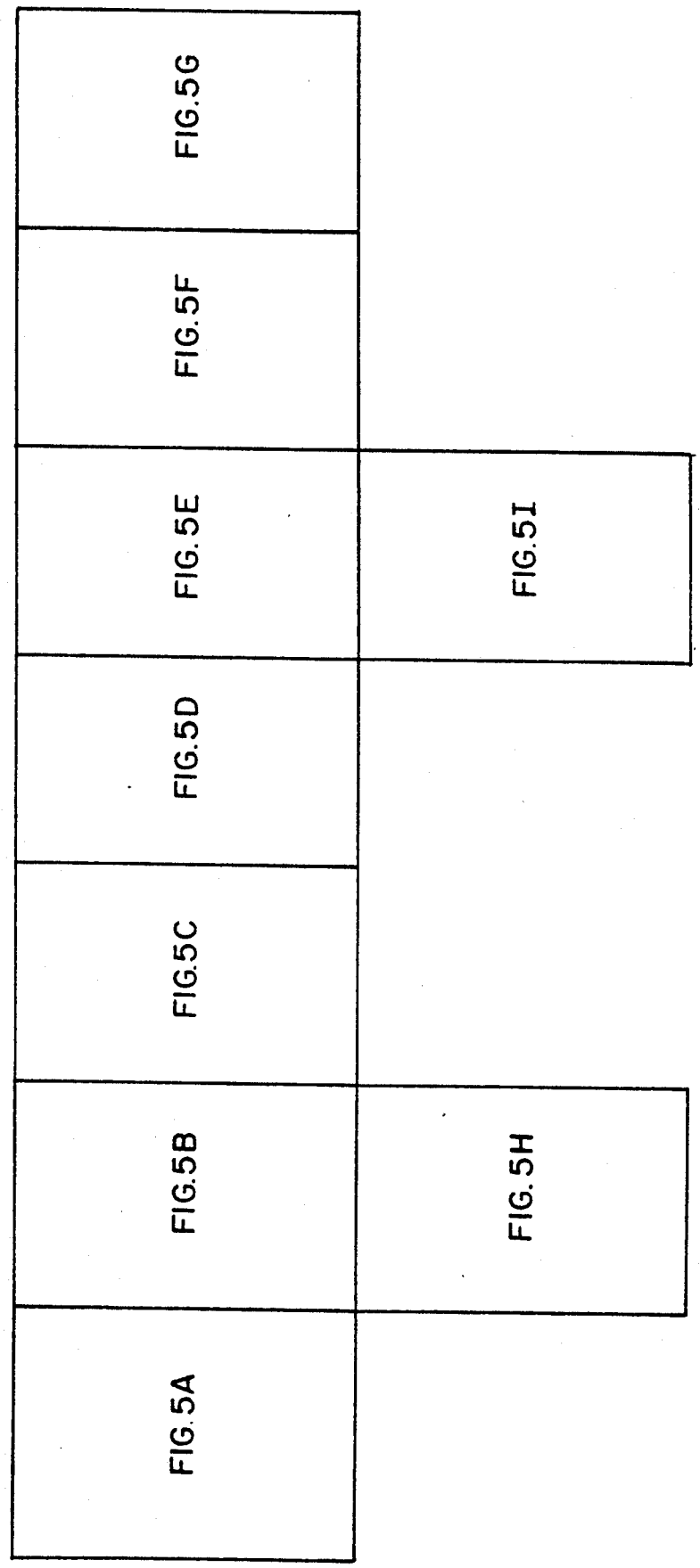
FIG. 6 is a diagrammatic showing of the placement of FIGS. 5A-5I in order to view these figures can be viewed as a whole.

As illustrated in FIG. 4, the second preferred detailed embodiment, like the more generalized illustration thereof shown in FIG. 3, is provided with a CPU 13 and its associated RAM 21 and ROM 22. If desired inputs and outputs to and from the CPU 13 may be fed to a monitor/recorder 20 which monitors and stores data, as in the detailed system shown in FIG. 3. The monitor/recorder 20 may also, as in the system of FIG. 3, effect a monitoring of the condition of the condition of the devices 14–19 and a history of actions effected.

The input side of the system, includes a plurality of physiologic signals, actually electric analogue signal representations of physiologic conditions, shown by way of example as $O_2$ level in mixed venous blood, pH of blood, cardiac output, pressure at one site in the circulatory system of the patient and pressure at another site in the circulatory system of the patient. Other possible signals could represent $CO_2$ level in blood, end tidal $CO_2$ level in blood, DP/dt, blood temperature, body temperature, respiratory rate and lactic acidosis, to name a few. The respective physiologic signals are converted into digital signals by respective analogue-to-digital converters 23a to 23n and supplied as distinct inputs to the CPU 13.

The system of FIG. 4 includes electrical signals derived from action of the patient's heart. The electrical signals, as illustrated, include an atrial signal, a ventricular signal and a plurality of EKG signals, which are obtained by conventional means. The respective electrical signals are fed to respective analogue-to-digital converters 24a–24n and are converted into respective digital signals which are fed, as distinct inputs, to the CPU 13.

The CPU 13 effects a comparison of one or more of the digital signal representations of the physiologic signals against a fixed (for example, as disclosed in U.S. Pat. No. 4,967,749) or a varying baseline (for example, as disclosed in U.S. Pat. No. 4,774,950) representations thereof, possibly after processing the signals into signals representing mean, systolic, diastolic, pulse pressures or the like. The CPU 13 also determines the pulse rate, R-wave, QRS complex (possibly against a "template" of the patient's QRS complex when the heart is functioning properly) and/or another morphologic basis, tachycardia acceleration, atrial-ventricular timing, ST segment analysis and the like.

The CPU 13, using programs stored in the ROM 21, determines if any of the malfunctions set out in FIGS. 5A–5I is present and produces control signals which are fed respectively to the antitachycardia pacemaker 14, to the antibradycardia pacemaker 15, to the cardioverter 16, to the defibrillator 17, to the respective drug delivery devices 18a–18d and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia. The diagnostic and treatment routines which are carried out by the central processing unit 13, with its associated RAM 21 and ROM 22, are set out in blocks 500–599 of FIGS. 5A–5I.

The pair of radio transmitter-receivers 25 and 26, as in the system shown in FIG. 3, provide a wireless link from the implantable portions of the system to a station outside the patient. The link not only allows one to retrieve data from the monitor/recorder 20, but also allows one to reprogram the CPU 13 and its associated RAM 21 and ROM 22 to effect resetting of the baselines, durations of the given (long term) baseline periods, duration of the predetermined (short term) baseline periods and the patient treatment routines.

Figure 7:
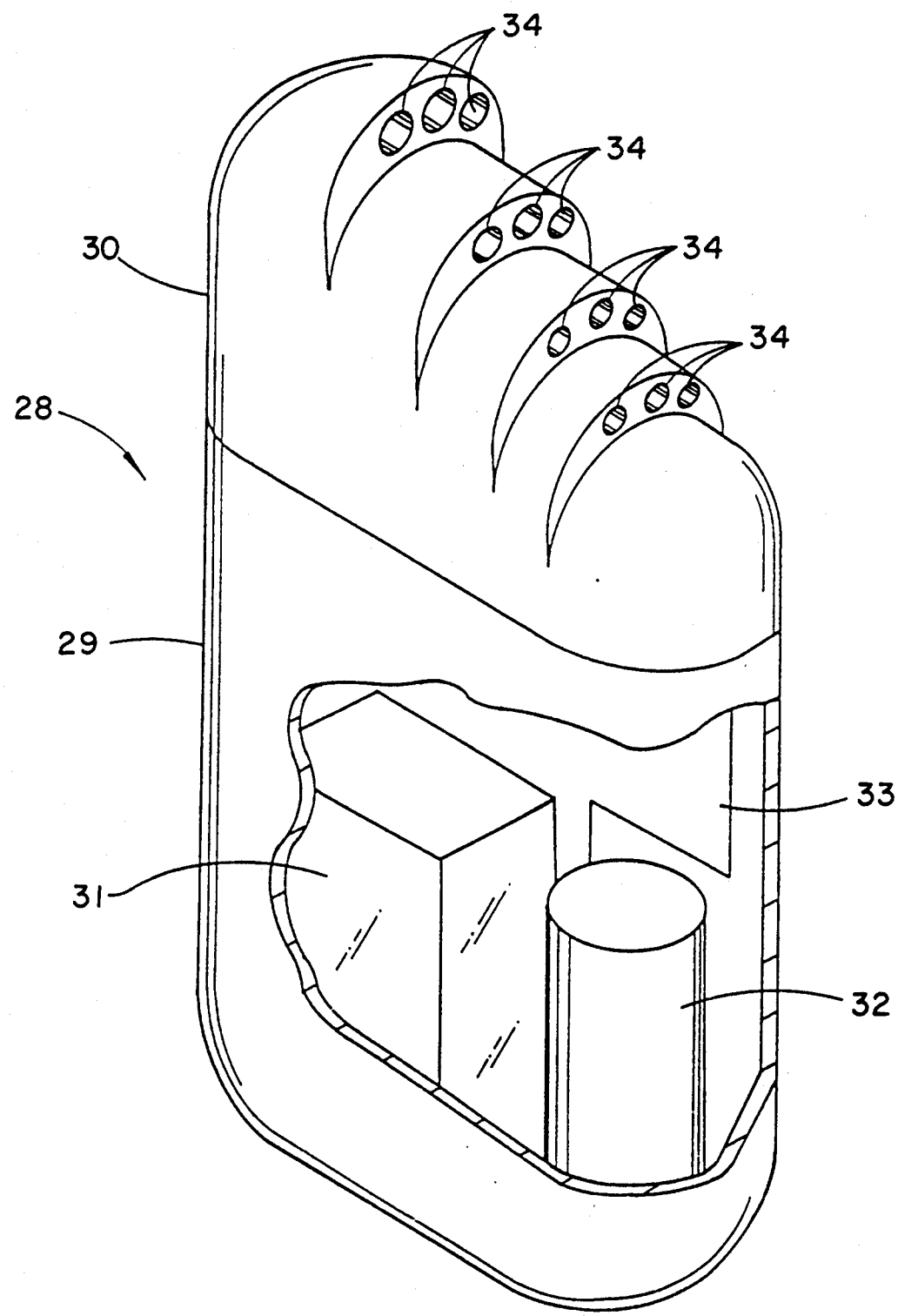
FIG. 7 is a pictorial illustration of an exemplary implantable controlled electrical energy pulse generator which may be used as a component of an implantable system shown in FIGS. 3 and 4, for treating a malfunctioning heart in accordance with the present invention, the housing of the generator being partially broken away to show positioning of major components thereof.

One possible general implantable configuration of a housing 28, which may be used in practicing the present invention, is shown in FIG. 7. The housing 28 includes a case 29, made of titanium, and a header 30, formed of an epoxy material, fixed to the case 29, all external components being hermetically sealed and biocompatible for human implantation. Within the case 28 is a battery pack or battery 31, an energy storage capacitor 32 and an electronic module 33 in or on which circuit components, other than the battery pack or battery 31 and the capacitor 32, are positioned. A plurality of openings 34 are provided in the header 30 for receiving inputs to the A/D converters 23a-23n and outputs from the devices 14-17 and inputs to the devices 18a-18d and 19. Those of the openings 34 which may not be utilized when providing to treat particular patients, may be closed by suitable plugs prior to implantation.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

I claim:

1. In an implantable system for treating the malfunctioning heart of a patient, the combination of means for deriving at least one electrical signal from the patient's heart, means for deriving at least one physiologic signal from or related to the patient's circulatory system, a central processing unit for controlling delivery of selected heart-malfunction-corrective inputs to the patient, means for inputting the at least one electrical signal and the at least one physiologic signal to the central processing unit, and output means responsive to output signals form the central processing unit, including cardioverting/defibrillating means, for providing under control of the central processing unit at least one heart-malfunction-corrective input to the patient from among a plurality of the heart-malfunction-corrective inputs, whereby malfunctions of the heart may be corrected.

2. The implantable system of claim 1, wherein the output means includes antitachycardia pacing means controlled by the central processing unit.

3. The implantable system of claim 1, wherein the output means includes antibradycardia pacing means controlled by the central processing unit.

4. The implantable system of claim 1, wherein the central processing unit is programmable.

5. The implantable system of claim 1, wherein the output means includes drug delivery means controlled by the central processing unit.

6. The implantable system of claim 1, wherein the output means includes a heart-assist device controlled by the central processing unit.

7. The implantable system of claim 1, further including monitoring means and/or recording means coupled to the central processing unit for monitoring and/or recording input and output signals to and from the central processing unit.

8. The implantable system of claim 1, wherein the output means further includes drug delivery means, antitachycardia pacing means and antibradycardia pacing means controlled by the central processing unit.

9. The implantable system of claim 1, wherein the output means further include antitachycardia pacing means and antibradycardia pacing means controlled by the central processing unit.

10. The implantable system of claim 1, wherein the output means further includes antibradycardia pacing means controlled by the central processing unit.

11. The implantable system of claim 1, including means for monitoring heart rhythm to develop the at least one electrical signal, and means responsive to the at least one electrical signal and to the at least one physiologic signal for identifying stable supraventricular tachycardia.

12. The implantable system of claim 11, which includes means for supplying therapy to the patient whereby stable supraventricular tachycardia may be overcome.

13. The implantable system of claim 1, including means for monitoring heart rhythm to develop the at least one electrical signal, and means responsive to the at least one electrical signal and to the at least one physiologic signal for identifying unstable supraventricular tachycardia.

14. The implantable system of claim 13, which includes means for supplying therapy to the patient whereby unstable supraventricular tachycardia may be overcome.

15. The implantable system of claim 1, including means for monitoring heart rhythm to develop the at least one electrical signal, and means responsive to the at least one electrical signal and to the at least one physiologic signal for identifying stable ventricular tachycardia.

16. The implantable system of claim 15, which includes means for supplying therapy to the patient whereby stable ventricular tachycardia may be overcome.

17. The implantable system of claim 1, including means for monitoring heart rhythm to develop the at least one electrical signal, and means responsive to the at least one electrical signal and to the at least one physiologic signal for identifying unstable ventricular tachycardia.

18. The implantable system of claim 17, which includes means for supplying therapy to the patient whereby unstable ventricular tachycardia may be overcome.

19. The implantable system of claim 1, including means for monitoring heart rhythm to develop the at least one electrical signal, and means responsible to the at least one electrical signal for identifying rapid ventricular tachycardia and ventricular fibrillation.

20. The implantable system of claim 19, which includes means for supplying therapy to the patient whereby rapid ventricular tachycardia and ventricular fibrillation may be overcome.

21. The implantable system of claim 1, including means for monitoring heart rhythm to develop the at least one electrical signal, and means responsive to at least one electrical signal and to the at least one physiologic signal for identifying rapid ventricular fibrillation.

22. The implantable system of claim 21, which includes means for supplying therapy to the patient whereby rapid ventricular fibrillation may be overcome.

23. The implantable system of claim 1, including means for monitoring heart rhythm to develop the at least one electrical signal, and means responsive to the at least one electrical signal and to the at least one physiologic signal for identifying asystole.

24. The implantable system of claim 23, which includes means for supplying therapy to the patient whereby asystole may be overcome.

25. The implantable system of claim 1, including means for monitoring heart rhythm to develop the at least one electrical signal, and means responsive to the at least one electrical signal and to the at least one physiologic signal for identifying stable bradycardia.

26. The implantable system of claim 25, which includes means for supplying therapy to the patient whereby stable bradycardia may be overcome.

27. The implantable system of claim 1, including means for monitoring heart rhythm to develop the at least one electrical signal, and means responsive to the at least one electrical signal and to the at least one physiologic signal for identifying unstable bradycardia.

28. The implantable system of claim 27, which includes means for supplying therapy to the patient whereby unstable bradycardia may be overcome.

29. The implantable system of claim 1, including means for monitoring heart rhythm to develop the at least one electrical signal, and means responsive to the at least one electrical signal and to the at least one physiologic signal for identifying ischemia.

30. The implantable system of claim 29, which includes means for supplying therapy to the patient whereby ischemia may be overcome.

31. The implantable system of claim 1, including means for monitoring heart rhythm to develop the at least one electrical signal, and means responsive to the at least one electrical signal and to the at least one physiologic signal for identifying early infarction.

32. The implantable system of claim 31, which includes means for supplying therapy to the patient whereby early infarction may be overcome.

33. The implantable system of claim 1, including means for monitoring heart rhythm to develop the at least one electrical signal, and means responsive to the at least one electrical signal and to the at least one physiologic signal for identifying heart failure alone.

34. The implantable system of claim 33, which includes means for supplying therapy to the patient whereby heart failure alone may be overcome.

35. The implantable system of claim 1, including means for monitoring heart rhythm to develop the at least one electrical signal, and means responsive to the at least one electrical signal and to the at least one physiologic signal for identifying stable supraventricular tachycardia, unstable supraventricular tachycardia, stable ventricular tachycardia, unstable ventricular tachycardia, stable atrial fibrillation, unstable atrial fibrillation, ventricular fibrillation, asystole, stable bradycardia, unstable bradycardia, ischemia, early infarction and heart failure alone.

36. The implantable system of claim 1, including means for monitoring heart rhythm to develop the at least one electrical signal, and means responsive to the at least one electrical signal and to the at least one physiologic signal for identifying stable supraventricular tachycardia, unstable supraventricular tachycardia, stable ventricular tachycardia, unstable ventricular tachycardia, stable atrial fibrillation, unstable atrial fibrillation, ventricular fibrillation, asystole, stable bradycardia, and unstable bradycardia.

37. The implantable system of claim 1, including means coupled to said means for deriving at least one physiologic signal and responsive thereto for determining a change in a given physiologic parameter of at least a predetermined magnitude from a baseline for the parameter as represented by the physiologic signal.

38. The implantable system according to claim 1, including means coupled to said means for deriving at least one physiologic signal and responsive thereto over a period of given duration for establishing a varying baseline for a given physiologic parameter as represented by the physiologic signal, and means coupled to said means for deriving at least one physiologic signal and responsive thereto for determining current level of the parameter as represented by the physiologic signal over a period of predetermined duration which is shorter than the period of given duration.

39. The implantable system according to claim 1, including means for adjustably setting a baseline for a given physiologic parameter as represented by the physiologic signal.

40. In a system for treating the malfunctioning heart of a patient, a combination of means for deriving at least one electrical signal from the patient's heart, means for deriving at least one physiologic signal from or related to the patient's circulatory system, means responsive to the physiologic signal for determining a change in a physiologic parameter of at least a predetermined magnitude from a baseline for the parameter, a central processing unit, means for inputting the at least one electrical signal and the at least one physiologic signal to the central processing unit, and output means coupled to the central processing unit and responsive to output signals therefor, including cardioverting/defibrillating means, for providing under control of the central processing unit at least one heart-malfunction-corrective input to the patient from among a plurality of the heart-malfunction-corrective inputs, whereby malfunctions of the heart may be corrected.

41. The system of claim 40, including means for monitoring heart rhythm to develop the at least one electrical signal, and means responsive to the at least one electrical signal and to the at least one physiologic signal for identifying stable supraventricular tachycardia.

42. The system of claim 41, which includes means for supplying therapy to the patient whereby stable supraventricular tachycardia may be overcome.

43. The system of claim 40, including means for monitoring heart rhythm to develop the at least one electrical signal, and means responsive to the at least one electrical signal and to the at least one physiologic signal for identifying unstable supraventricular tachycardia.

44. The system of claim 43, which includes means for supplying therapy to the patient whereby unstable supraventricular tachycardia may be overcome.

45. The system of claim 40, including means for monitoring heart rhythm to develop the at least one electrical signal, and means responsive to the at least one electrical signal and to the at least one physiologic signal for identifying stable ventricular tachycardia.

46. The system of claim 45, which includes means for supplying therapy to the patient whereby stable ventricular tachycardia may be overcome.

47. The system of claim 40, including means for monitoring heart rhythm to develop the at least one electrical signal, and means responsive to the at least one electrical signal and to the at least one physiologic signal for identifying unstable ventricular tachycardia.

48. The system of claim 47, which includes means for supplying therapy to the patient whereby unstable ventricular tachycardia may be overcome.

49. The system of claim 40, including means for monitoring heart rhythm to develop the at least one electrical signal, and means responsible to the at least one electrical signal for identifying rapid ventricular tachycardia and ventricular fibrillation.

50. The system of claim 49, which includes means for supplying therapy to the patient whereby rapid ventricular tachycardia and ventricular fibrillation may be overcome.

51. The system of claim 40, including means for monitoring heart rhythm to develop the at least one electrical signal, and means responsive to at least one electrical signal and to the at least one physiologic signal for identifying rapid ventricular fibrillation.

52. The system of claim 51, which includes means for supplying therapy to the patient whereby rapid ventricular fibrillation may be overcome.

53. The system of claim 40, including means for monitoring heart rhythm to develop the at least one electrical signal, and means responsive to the at least one electrical signal and to the at least one physiologic signal for identifying asystole.

54. The system of claim 53, which includes means for supplying therapy to the patient whereby asystole may be overcome.

55. The system of claim 40, including means for monitoring heart rhythm to develop the at least one electrical signal, and means responsive to the at least one electrical signal and to the at least one physiologic signal for identifying stable bradycardia.

56. The system of claim 55, which includes means for supplying therapy to the patient whereby stable bradycardia may be overcome.

57. The system of claim 40, including means for monitoring heart rhythm to develop the at least one electrical signal, and means responsive to the at least one electrical signal and to the at least one physiologic signal for identifying unstable bradycardia.

58. The system of claim 57, which includes means for supplying therapy to the patient whereby unstable bradycardia may be overcome.

59. The system of claim 40, including means for monitoring heart rhythm to develop the at least one electrical signal, and means responsive to the at least one electrical signal and to the at least one physiologic signal for identifying ischemia.

60. The system of claim 59, which includes means for supplying therapy to the patient whereby ischemia may be overcome.

61. The system of claim 40, including means for monitoring heart rhythm to develop the at least one electrical signal, and means responsive to the at least one electrical signal and to the at least one physiologic signal for identifying early infarction.

62. The system of claim 61, which includes means for supplying therapy to the patient whereby early infarction may be overcome.

63. The system of claim 40, including means for monitoring heart rhythm to develop the at least one electrical signal, and means responsive to the at least one electrical signal and to the at least one physiologic signal for identifying heart failure alone.

64. The system of claim 63, which includes means for supplying therapy to the patient whereby heart failure alone may be overcome.

65. The combination according to claim 40, including means responsive to the physiologic signal over a period of given duration for establishing a varying baseline for the parameter, and means responsive to the physiologic signal for determining current level of the parameter over a period of predetermined duration which is shorter than said period of given duration.

66. The combination according to claim 40, including means for adjustably setting the baseline for the physiologic parameter.

67. The system according to claim 40, which is adapted to be implanted in a patient.

68. The implantable system of claim 67, including means for monitoring heart rhythm to develop the at least one electrical signal, and means responsive to the at least one electrical signal and to the at least one physiologic signal for identifying stable supraventricular tachycardia.

69. The implantable system of claim 68, which includes means for supplying therapy to the patient whereby stable supraventricular tachycardia may be overcome.

70. The implantable system of claim 67, including means for monitoring heart rhythm to develop the at least one electrical signal, and means responsive to the at least one electrical signal and to the at least one physiologic signal for identifying unstable supraventricular tachycardia.

71. The implantable system of claim 70, which includes means for supplying therapy to the patient whereby unstable supraventricular tachycardia may be overcome.

72. The implantable system of claim 67, including means for monitoring heart rhythm to develop the at least one electrical signal, and means responsive to the at least one electrical signal and to the at least one physiologic signal for identifying stable ventricular tachycardia.

73. The implantable system of claim 22, which includes means for supplying therapy to the patient whereby stable ventricular tachycardia may be overcome.

74. The implantable system of claim 67, including means for monitoring heart rhythm to develop the at least one electrical signal, and means responsive to the at least one electrical signal and to the at least one physiologic signal for identifying unstable ventricular tachycardia.

75. The implantable system of claim 74, which includes means for supplying therapy to the patient whereby unstable ventricular tachycardia may be overcome.

76. The implantable system of claim 67, including means for monitoring heart rhythm to develop the at least one electrical signal, and means responsible to the at least one electrical signal for identifying rapid ventricular tachycardia and ventricular fibrillation.

77. The implantable system of claim 76, which includes means for supplying therapy to the patient whereby rapid ventricular tachycardia and ventricular fibrillation may be overcome.

78. The implantable system of claim 67, including means for monitoring heart rhythm to develop the at least one electrical signal, and means responsive to at least one electrical signal and to the at least one physiologic signal for identifying rapid ventricular fibrillation.

79. The implantable system of claim 78, which includes means for supplying therapy to the patient whereby rapid ventricular fibrillation may be overcome.

80. The implantable system of claim 67, including means for monitoring heart rhythm to develop the at least one electrical signal, and means responsive to the at least one electrical signal and to the at least one physiologic signal for identifying asystole.

81. The implantable system of claim 80, which includes means for supplying therapy to the patient whereby asystole may be overcome.

82. The implantable system of claim 67, including means for monitoring heart rhythm to develop the at least one electrical signal, and means responsive to the at least one electrical signal and to the at least one physiologic signal for identifying stable bradycardia.

83. The implantable system of claim 82, which includes means for supplying therapy to the patient whereby stable bradycardia may be overcome.

84. The implantable system of claim 67, including means for monitoring heart rhythm to develop the at least one electrical signal, and means responsive to the at least one electrical signal and to the at least one physiologic signal for identifying unstable bradycardia.

85. The implantable system of claim 84, which includes means for supplying therapy to the patient whereby unstable bradycardia may be overcome.

86. The implantable system of claim 67, including means for monitoring heart rhythm to develop the at least one electrical signal, and means responsive to the at least one electrical signal and to the at least one physiologic signal for identifying ischemia.

87. The implantable system of claim 86, which includes means for supplying therapy to the patient whereby ischemia may be overcome.

88. The implantable system of claim 67, including means for monitoring heart rhythm to develop the at least one electrical signal, and means responsive to the at least one electrical signal and to the at least one physiologic signal for identifying early infarction.

89. The implantable system of claim 88, which includes means for supplying therapy to the patient whereby early infarction may be overcome.

90. The implantable system of claim 67, including means for monitoring heart rhythm to develop the at least one electrical signal, and means responsive to the at least one electrical signal and to the at least one physiologic signal for identifying heart failure alone.

91. The implantable system of claim 90, which includes means for supplying therapy to the patient whereby heart failure alone may be overcome.

92. The combination according to claim 67, including means responsive to the physiologic signal over a period of given duration for establishing a varying baseline for the parameter, and means responsive to the physiologic signal for determining current level of the parameter over a period of predetermined duration which is shorter than said period of given duration.

93. The combination according to claim 67, including means for adjustably setting the baseline for the physiologic parameter.

94. Apparatus for treating a malfunctioning heart of a patient by supplying cardioverting/defibrillating energy to the patient to overcome or avoid hemodynamic comprise and avoid consequent death of the patient who may be exhibiting sudden death syndrome, comprising computerized means having at least a first input and a second input, and at least one output, means for obtaining an electrical signal from the patient's heart and for feeding that electrical signal to the first input of the computerized means, means for monitoring at least one selected parameter of the patient's circulatory system to develop a physiologic signal representation thereof, means for feeding the physiologic signal to the second input, means within the computer means for establishing a baseline for the selected parameter of the patient to develop a baseline signal representation thereof, comparison means within said computerized means for comparing the baseline signal on a short term basis with the physiological signal, cardioverting/defibrillating means for delivering cardioverting/defibrillating energy to the patient, and means coupled to and responsive to the output from the computerized means for triggering the cardioverting/defibrillating means to thereby provide cardioverting/defibrillating energy to the patient's heart to avoid or overcome hemodynamic comprise of the patient.

95. The apparatus of claim 94, wherein the computerized means comprises a programmable microprocessor.

96. The apparatus of claim 94, wherein the means for monitoring at least one selected parameter comprises means for monitoring pressure in the patient's circulatory system.

97. The apparatus of claim 94, wherein the means for monitoring at least one selected parameter comprises means for monitoring pressure in the right atrium of the patient's heart.

98. The apparatus of claim 94, wherein the selected parameter is oxygen saturation in mixed venous blood.

99. The apparatus of claim 94, wherein the selected parameter is potassium ion level in the patient's blood.

100. The apparatus of claim 94, wherein the selected parameter is lactic acid in the patient's blood.

101. The apparatus of claim 94, wherein the means for establishing a baseline comprises means for establishing a long-term variable baseline of the selected parameter.

102. The apparatus of claim 94, wherein the apparatus is an implantable apparatus which is adapted to be implanted in its entirety into the patient.

103. The apparatus of claim 94, wherein the apparatus is adapted to be at least partially external to the patient.

104. The apparatus of claim 94, further including antibradycardia pacing means, antitachycardia pacing means and drug delivery devices, and means for selectively energizing the antibradycardia pacing means, the antitachycardia pacing means and the drug delivery devices.

* * * * *